United States Patent
Kumagai et al.

(10) Patent No.: US 6,984,493 B1
(45) Date of Patent: Jan. 10, 2006

(54) METHOD FOR EXAMINING THE INVOLVEMENT OF OPIOID PEPTIDES IN PRURTIS

(75) Inventors: Hiroo Kumagai, Tokyo (JP); Takao Saruta, Tokyo (JP)

(73) Assignee: Toray Industries, Inc., (JP)

( * ) Notice: Subject to any disclaimer, the term of this patent is extended or adjusted under 35 U.S.C. 154(b) by 0 days.

(21) Appl. No.: 09/704,319

(22) Filed: Nov. 2, 2000

(30) Foreign Application Priority Data

May 8, 2000  (JP)  ............................. 2000/135043

(51) Int. Cl.
  *G01N 33/53*   (2006.01)
  *G01N 33/567*  (2006.01)
  *A61K 38/00*   (2006.01)
  *A61K 35/16*   (2006.01)
  *C07K 14/00*   (2006.01)

(52) U.S. Cl. .................. 435/7.1; 435/7.2; 530/300; 424/531

(58) Field of Classification Search ................. 435/7.1, 435/7.2, 531; 530/300
See application file for complete search history.

(56) References Cited

OTHER PUBLICATIONS

Simonnet G, et al. Neuropeptides Apr. 1986; 7(3):229-40.*
Ripamonti C, et al. Ann Oncol Jan. 1998; 9(1):79-83.*

* cited by examiner

*Primary Examiner*—Robert S. Landsman
(74) *Attorney, Agent, or Firm*—DLA Piper Rudnick Gray Cary US LLP (57) ABSTRACT

A method for examining a disease includes measuring plural opioid peptides or opioid receptors in blood cell, body fluid, or tissue and calculating the ratio thereof. The method can be specifically applied to pruritic diseases. The invented method for examination can determine whether opioids are involved in a pruritic disease and can determine whether therapy with an opioid agonistic and/or antagonistic antipruritus agent is appropriate or not.

4 Claims, 3 Drawing Sheets

METHOD FOR EXAMINING THE INVOLVEMENT OF OPIOID PEPTIDES IN PRURTIS

BACKGROUND OF THE INVENTION

1. Field of the Invention

The present invention relates to a method for examining the involvement of opioids in diseases.

2. Description of the Related Art

Recently, it has become evident that opioids have a wide variety of biological activities. For examples, opioids are not only involved in pain, but also act upon the immune system (T. Hosokawa et al., Pain Clinic, 21, 857–864, 2000). However, roles which the opioids play in vivo have not been sufficiently clarified other than those in pain. For example, the relation of the opioids with itching (pruritus) is now being clarified, while itching is considered to be close to pain.

Itching (pruritus) is a sensation which is unique to skin, and is mostly observed in a variety of dermatoses attended with inflammation. However, such itching is also induced by some internal diseases (e.g., malignant tumor, diabetes, hepatic diseases, renal failure, hemodialysis, peritoneal dialysis, gout, diseases of the thyroid, blood disorders, and sideropenia) or by pregnancy or vermination. In addition, it is sometimes caused by medicaments or is psychogenically caused. Itching is a subjective sensation and cannot be objectively quantitatively assessed. How and in which mechanism itching manifests has not yet been sufficiently clarified.

For pruritus therapy, antihistaminic agents or antiallergic agents are mainly used as oral medicines, and antihistaminic agents, adrenocortic steroidal medicines for external application, nonsteroidal antiphlogistics, camphor, menthol, phenol, salicylic acid, rectified tar oil, crotamiton, capsaicin, moisture-retentive agents (e.g., urea, Hirudoid (trade name; a heparinoid from animal organs, available from Maruho Co., Ltd.), and Vaseline). Of these therapeutic agents, only antihistaminic agents against urticaria are accepted to have a sufficient therapeutic efficacy. Other agents are not always sufficient in therapeutic efficacy in many cases (Y. Miyaji, Itching Q & A, p. 20, 1997, Iyaku (Medicine and Drug) Journal Co., Ltd.). The reason for this phenomenon is that inflammatory mediators such as histamine have been considered to be a main cause of itching, and antihistaminic agents and antiallergic agents serving as antagonists against these mediators have therefore been developed as therapeutic agents for pruritus.

At present, histamine, serotonin, substance P, bradykinin, proteinases, prostaglandins, and opioid peptides are known as stimulators to initiate itching. The itching sensation is considered to be initiated by the following mechanism. Specifically, itching stimulators act upon nerve endings (itching receptors) which reside in the epidermis-dermis interface, are composed of C fibers and are responsible to multi-stimulation. The resulting impulses are transmitted to afferent C fibers and reach the spinothalamic tract, thalamus and cerebral cortex in this order to induce itching (Y. Miyaji; Approach to Treatment of Skin Pruritus, p. 22, 1996, Sentan-Igaku (Advanced Medicine) Co Ltd.).

Some opioids have been known to be involved in inducement of itching. For example, it has been reported that endogenous opioids such as β-endorphin and enkephalin induce itching (B. Fjeller; Acta, Dermato-Venereol., 61 (suppl. 97), 1–34, 1981). In addition, it has been clarified that the epidural or intraspinal administration of morphine or an opioid compound initiates itching as an adverse drug reaction (J. H. Jaffe and W. R. Martin; Goodman and Gilman's Pharmacological Basis of Therapeutics, Macmillan, N.Y., 1985). On the other hand, it has been clarified that itching initiated by the intraspinal administration of morphine is inhibited by naloxone, a morphine antagonist (J. Bernstein et al.; J. Invest. Dermatol., 78, 82–83, 1982) and that a severe itching in a patient with hepatopathic cholestasia, which is firmly suggested to be induced by an increased enkephalin, is inhibited by an opioid antagonist nalmefene (J. R. Thornton and M. S. Losowsky; Br. Med. J., 297, 1501–1504, 1988). It is therefore the consensus view that opioid agonists act to initiate itching and, in contrast, opioid antagonists have an antipruritic activity. In addition, it has been reported that the serum concentrations of β-endorphin in children with atopic dermatitis are significantly higher than those in healthy children and that opioid antagonists may be effective against itching (S. Georgala et al.; J. Dermatol. Sci., 8, 125–128, 1994).

Based on these findings, itching is considered to be caused by chemical mediators such as histamine in some cases and by opioids such as morphine, β-endorphin, and other $\mu$ (mu) opioid receptor agonists or $\mu$-opioid peptides in other cases (K. Takamori; Dermatological Diagnosis and Treatment Practice 6: Atopic Dermatitis, p. 79, 1999, Bunkodo Co., Ltd.).

As such opioid receptors, $\mu$-, $\kappa$- (kappa), $\delta$- (delta), and ORL-1 (nociceptin) receptors are known, and endogenous opioid peptides that respectively selectively stimulate individual receptors have been found. For example, $\mu$- and $\delta$-receptor agonistic endogenous opioid peptides include β-endorphin and enkephalin, respectively, and $\kappa$-receptor agonistic endogenous opioid peptides include dynorphin, and ORL-1 receptor agonistic endogenous opioid peptides include nociceptin. Of these opioid peptides, α-endorphin is known as an opioid peptide which possibly invites itching. In contrast, $\kappa$-opioid agonists have been found to inhibit itching in recent years (PCT International Publication No. 98/23290), suggesting a possibility that $\kappa$-receptor agonistic endogenous peptides inhibit itching.

As described above, histamine and other chemical mediators, and opioids are considered to be candidates of causes of itching, and a therapy should be naturally selected depending on the cause. However, a method for selecting an appropriate therapy depending on the cause of itching has not yet been found.

SUMMARY OF THE INVENTION

Accordingly, it is an object of the present invention to clarify the involvement of opioids in various diseases, for example to clarify the pathoses (conditions) of pruritic diseases in which opioids are involved, to thereby provide a method for examining a disease to perform an appropriate therapy.

When opioids are involved in the itching pathosis, it is supposed that $\mu$-opioids ($\mu$-opioid peptides or expression of $\mu$-opioid receptors) are facilitated more than $\kappa$-opioids ($\kappa$-opioid peptides or expression of $\kappa$-opioid receptors). The $\mu$-opioids have the possibility of inviting itching, and the $\kappa$-opioids have the possibility of suppressing itching. We intensively investigated a concept that the relation between opioids and itching can be clarified by measuring the concentrations of opioids or degrees of expression of opioid receptors in blood cell, body fluid, or tissue to thereby verify that $\mu$-agonistic substances have the advantage over $\kappa$-opioid agonistic substances or that $\mu$-opioid receptors have the advantage over κ-opioid receptors. The present invention has been accomplished on the basis of these investigations and resulting findings.

In addition, the present invention can be naturally applied to examination of a variety diseases, as opioids are involved in various diseases.

Specifically, the present invention provides, in an aspect, a method for examining a disease. This method includes measuring the concentrations of plural opioid peptides in blood cell, body fluid, or tissue, and calculating the ratio of the concentrations to thereby determine whether opioids are involved in the disease. In another aspect, the present invention provides a method for examining a disease. The method includes measuring the degrees of expression of plural opioid receptors in blood cell, body fluid, or tissue, and comparing the degrees of expression to thereby determine whether opioids are involved in the disease.

DESCRIPTION OF THE PREFERRED EMBODIMENTS

According to the present invention, whether opioids are involved in a disease is determined by measuring the concentrations of plural opioids in blood cells, body fluid, or tissue and calculating the ratio of the concentrations, or by measuring the degrees of expression of plural opioid receptors and comparing the degrees of expression. Specifically, whether opioids are involved in a disease is determined by measuring the concentrations of plural opioids selected from μ-, κ-, δ-, and ORL-1 receptor agonistic endogenous peptides in sampled blood cells, body fluid, or tissue and determining the ratio of the concentrations, or by measuring degrees of expression of plural opioid receptors selected from β-, κ-, δ-, and ORL-1 opioid receptors and comparing the measured degrees of expression.

Samples for use in measurement of the concentrations of opioid peptides or the degrees of expression of opioid receptors include, but are not limited to, white blood cells, red blood cells, and other blood cell components; blood plasma, saliva, sweat, intraspinal fluid, and other body fluids; skin, oral mucosa, and other tissues that can be relatively easily sampled, tissues that are available as biopsy specimens or specimens taken by operative extirpation, and other available tissues. Of these samples, blood plasma sampled from a subject is preferably employed for the measurement of the opioid peptide concentrations, and peripheral blood mononuclear cell (monocyte) is preferably employed for the measurement of the degrees of expression of the opioid receptors.

The opioid peptides to be measured include, for example, β-endorphin, endomorphin-1, endomorphin-2, and other μ-receptor agonistic endogenous peptides; leucine enkephalin (Leu-enkephalin), methionine enkephalin (Met-enkephalin), and other δ-receptor agonistic endogenous peptides; dynorphin A, dynorphin B, dynorphin-associated peptides, and other κ-receptor agonistic endogenous peptides; and nociceptin, and other ORL-1 receptor agonistic endogenous peptides. The opioid peptides also include the other endogenous peptides which have activities upon the aforementioned receptors. Such endogenous peptides include α-endorphin, γ-endorphin, and other endorphin-associated peptides; α-neoendorphin, β-neoendorphin, rimorphin, and other dynorphin-associated peptides; and casomorphin which is a lysate of casein protein. Of these substances, μ-receptor agonistic endogenous opioid peptides and κ-receptor agonistic endogenous opioid peptides are preferably subjected to the measurement of concentrations to thereby determine whether opioids are involved in pruritus, of which β-endorphin and dynorphin A are typically preferably subjected to the measurement of concentrations.

The concentrations of opioid peptides in body fluids can be measured by, for example, radioimmunoassay (RIA), enzyme-linked immunosorbent assay (EIA) or chromatography. The concentrations of opioid peptides in blood cells or tissue can be measured by extracting target substances from blood cells or tissue and measuring the concentrations through any of the above assays or by extracting total RNA or mRNA from blood cells or tissue and measuring the expression of peptide molecules by RT-PCR (reverse transcriptase-PCR) or other molecular-biological techniques. Such radio-immunoassay, enzyme-linked immunosorbent assay, chromatography, RT-PCR, and other techniques for use in the measurement can be performed in a conventional manner.

As the measurement of degrees of expression of opioid receptors to determine whether the opioids are involved in pruritus, the degrees of expression of a μ-opioid receptor and a κ-opioid receptor should be preferably measured.

The degrees of expression of opioid receptors are preferably measured by a process of extracting total RNA or mRNA in a specimen and measuring the degrees through RT-PCR method (reverse-transcriptase-PCR method) or other molecular-biological techniques. The degrees of expression of receptor molecules can also be measured by an immunochemical technique using antibodies against the receptors or by the receptor binding method using labeled ligands for individual receptors. For example, in the measurement by the RT-PCR method, the degrees of expression of receptors can be scored using intensities of bands obtained through electrophoresis as indexes. The RT-PCR method, immunochemical technique using antibodies against receptors, receptor binding method, and other techniques for use in the measurement can be performed in a conventional manner.

The concentrations of opioid peptides and the degrees of expression of opioid receptors can be measured by any technique as far as they can qualitatively or quantitatively measure the expression of opioid receptors substantially, and they are not limited to the aforementioned techniques.

From these measurements, whether opioids are involved in a disease can be determined by calculating the ratio of concentrations of different opioid peptides or by comparing the degrees of expression of different opioid receptors. Specifically, whether opioids are involved in a pathosis (condition) can be determined, for example, through indications that the concentration of a specific opioid peptide in a patient with a disease is higher than, or lower than the other opioid peptides as compared with healthy adults or that the degree of expression of a specific opioid receptor is higher than, or lower than the degrees of expression of the other opioid receptors.

For example, when the involvement of opioids in pruritus is to be determined, the ratio of the concentrations of different opioid peptides is calculated or the degrees of expression of different opioid receptors are compared with each other in cases with itching, to thereby verify that a μ-agonistic opioid peptide has the advantage over a κ-agonistic opioid peptide in blood cells, body fluid, or tissue or that the degree of expression of a μ-opioid receptor has the advantage over a κ-opioid receptor. Examples of indications for the determination are that the plasma concentration of a μ-agonistic opioid peptide is higher than that of healthy adults, that the concentration of a μ-agonistic opioid peptide is relatively higher than that of healthy adults when the concentration of a κ-agonistic opioid peptide and that of the μ-agonistic opioid peptide are compared, and that the representation of a μ-agonistic opioid peptide in tissue is relatively higher than that of healthy adults when the representation of the μ-agonistic opioid peptide and that of a κ-agonistic opioid peptide are compared. Regarding the opioid receptors, an indication for determination is, for example, that the degree of expression of a μ-receptor in blood cell component or in tissue is relatively higher than that of a κ-receptor as compared with healthy adults: In addition, whether opioids are involved in itching can be comprehensively determined by considering the concentrations or the ratio thereof of endogenous opioid peptides in blood cells, body fluid, or tissue, as well as the degrees of expression of opioid receptors in blood cells, body fluid or tissue.

In this connection, there is a possibility that δ-opioid agonistic enkephalin, and δ-opioid receptors, as well as nociceptin and ORL-1 (nociceptin) receptors are also involved in itching. These substances can also be subjected to measurement according to the above technique and the results can be used as references for the determination.

When it is determined that opioids are greatly involved in the itching pathosis (condition), the subject or patient can be subjected to a therapy for inhibiting itching, such as the administration of an antagonist against μ-opioid receptor, a treatment for inhibiting the synthesis of a μ-agonistic opioid peptide such as β-endorphin, or the administration of a κ-opioid agonist. For example, an apparent antipruritic effect can be obtained by the administration of a κ-opioid agonist 17-cyclopropylmethyl-3,14β-dihydroxy-4,5α-epoxy-6β-[N-methyl-trans-3-(3-furyl)acrylamide] morphinan disclosed in PCT International Publication No. 98/23290, as shown in Example 2 below.

Diseases to which the present invention is applied include, but are not limited to, diseases with pain or itching, immunological diseases, inflammatory diseases, neuropathy, and metabolic diseases. Particularly, diseases with pruritus include, but are not limited to, atopic dermatitis, neurodermatitis, contact dermatitis, seborrheic dermatitis, autosensitization dermatitis, caterpillar dermatitis, asteatosis, senile pruritus, insect bite, hyperesthesia optica, urticaria, prurigo, herpes, impetigo, eczema, tinea, lichen, psoriasis, scabies, acne vulgaris, and other dermatoses, malignant tumor, diabetes, hepatic disease, renal failure, hemodialysis, peritoneal dialysis, and other internal diseases, and pruritus with pregnancy. The present invention is particularly effectively applied to the examination of pruritus with renal failure.

The present invention will be further illustrated in detail with reference to several examples below, which are not intended to limit the scope of the invention.

EXAMPLES

Example 1

[Preparation of Expression Analysis System of Human Opioid Receptor]

(1) Preparation of Human Opioid μ-Receptor Primer

Figure 1:
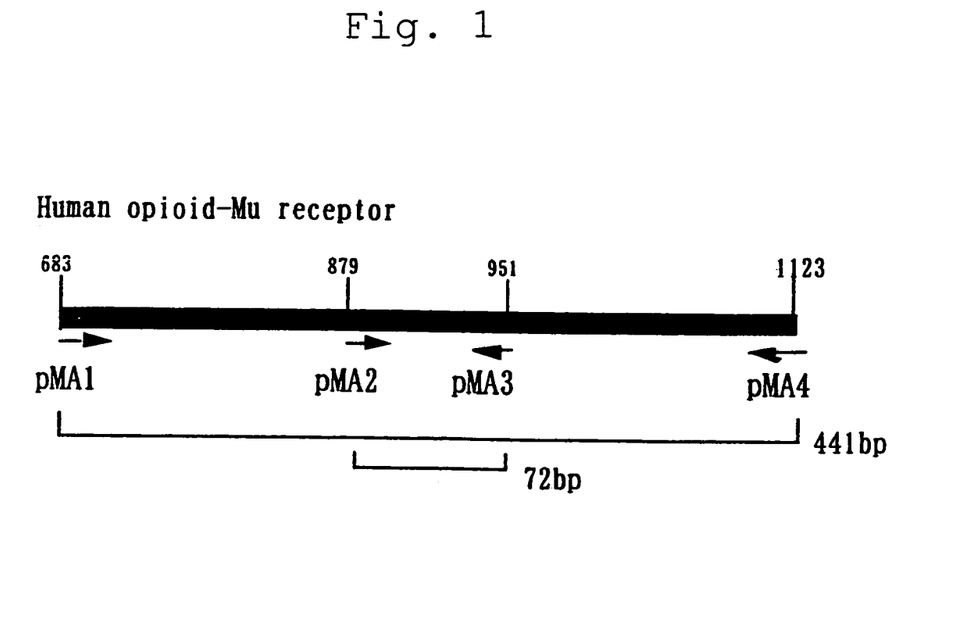
FIG. 1 illustrates combinations of primers and sizes of the resulting amplified DNAs when a human opioid preceptor gene is amplified by polymerase chain reaction (PCR)

Primers pMA1, pMA2, pMA3, and pMA4 each having a base sequence indicated in Table 1 were synthetically prepared according to the method described by T. K. Chuang, L. Yu et al. in Biochem. Biophis. Res. Comm., 216, 922–930 (1995). FIG. 1 shows combinations of the primers in PCR and the sizes of amplified DNAs.

TABLE 1

(SEQ ID NOS 1-4, respectively, in order of appearance)

| Name | Sequence of sense primer | Sequential location |
|---|---|---|
| pMA1 | 5'-GGT-ACT-GGG-AAA-ACC-TGC-TGA-AGA-TCT-GTG-3' | 683–712 |
| pMA2 | 5'-TGC-TGG-ACT-CCC-ATT-CAC-ATT-3' | 879–900 |
|  | Sequence of antisense primer |  |
| pMA3 | 5'-AGT-CTG-GAA-CGT-AGT-TTC-TGG-3' | 931–951 |
| pMA4 | 5'-GGT-CTC-TAG-TGT-TCT-GAC-CAA-TTC-GAG-TGG-3' | 1094–1123 |

The name, sequence, and location of primer where Adenin of initiation codon is defined as 1.

(2) Preparation of Human Opioid κ-Receptor Primer

Figure 2:
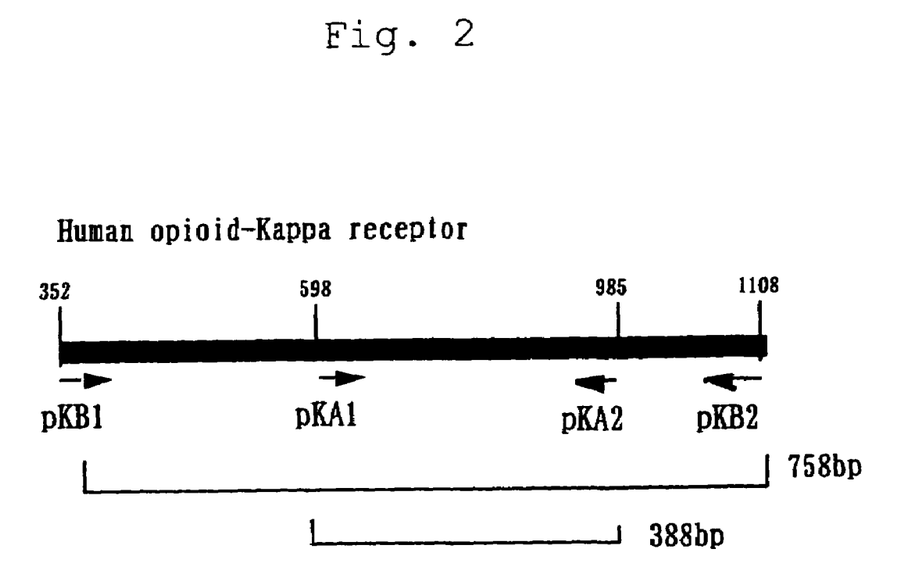
FIG. 2 illustrates combinations of primers and sizes of the resulting amplified DNAs when a human opioid κ-receptor gene is amplified by polymerase chain reaction (PCR)

Primers pKA1, pKB1, pKA2, and pKB2 each having a base sequence indicated in Table 2 were synthetically prepared according to the methods described by C. Gaveriaux, B. Kieffer et al. in FEBS Lett., 369, 272–276 (1995) and by L. F. Chuang, L. Yu et al. in Biochem. Biophis. Res. Commn., 209, 1003–1010 (1995). FIG. 2 shows combinations of the primers in PCR and the sizes of amplified DNAs.

TABLE 2

SEQ ID NOS 5-8, respectively, in order of appearance)

| Name | Sequence of sense primer | Sequential location |
|---|---|---|
| pKA1 | 5'-AAA-GTC-AGG-GAA-GAC-GTC-GAT-GTC-3' | 598–621 |
| pKB1 | 5'-GAG-AGC-TCG-CGG-CGC-GTC-TAG-TTG-ATG-AAT-TCC-TGG-3' | 352–372 |
|  | Sequence of antisense primer |  |
| pKA2 | 5'-GAA-TGG-GAT-TCA-GGC-TAC-TGT-TGG-3' | 962–985 |
| pKB2 | 5'-GGA-AGC-TTG-AAT-TCG-GTA-AGC-AGG-ATC-CTG-AAC-TG-3' | 1088–1108 |

The name, sequence, and location of primer where Adenine of initiation codon is defined as 1.

(3) Preparation of Expression Analysis System of Human Opioid μ- and κ-Receptors (a) Cultivation of Control Cell Human μ-receptor stable expression cells (Mu/CHO) and human κ-receptor stable expression cells (Kappa/CHO) were prepared, as positive control cells, according to a conventional technique. Separately, CHO cell was transformed only with an expression vector pCR3 to yield a transformed CHO cell ((−)/CHO) as a negative control cell. These cells were respectively cultivated in a nucleic acid-containing minimum essential medium α (α-MEM) (available from GIBCO, BRL) containing 10% (v/v) fetal calf serum (available from Biological Industries) at 37° C. in the presence of 5% $CO_2$.

(b) Recovery of Cells

Cells of about 80% confluent were washed with phosphate buffered saline (−) (PBS(−); available from Nissui Pharmaceutical Co., Ltd.) and were peeled off from a cultivator using a cell-scraper. The cells were then suspended in PBS (−) and were recovered through refrigerated centrifugation (3000 rpm, 5 minutes).

(c) Extraction of Total RNA, RT-PCR, and Analysis of Amplified DNA

Total RNA was extracted from each cell by acid guanidium-thiocyanate phenol-chloroform method (AGPC method) using R-Kit (trade name; available from Sumitomo Metal Industries, Ltd.) and was subjected to colorimetry. As a template, 1 μg of the total RNA was subjected to a reaction with 100 pmol of random primer using a reverse transcription (RT) enzyme Super Script II (trade name; available from GIBCO BRL) in 20 μL of a reaction mixture at 37° C. for 2 hours to yield cDNA. Using the prepared cDNA (the RT reaction mixture 1 μL) as a template, 200 μM of DNTP, 1.25 U of AmpliTaq (trade name; available from Perkin Elmer) (which reacts with Taq start antibody (available from Clonetech) in a ratio of 1:1), and 30 pmol of each primer were subjected to PCR in 50 μL of a reaction mixture. A 10× buffer supplied with AmpliTaq was used in PCR. PCR was performed according to a hot start technique while varying the number of cycles, and an annealing temperature. The resulting amplified DNAs were analyzed through agarose gel electrophoresis according to a conventional technique.

Figure 3:
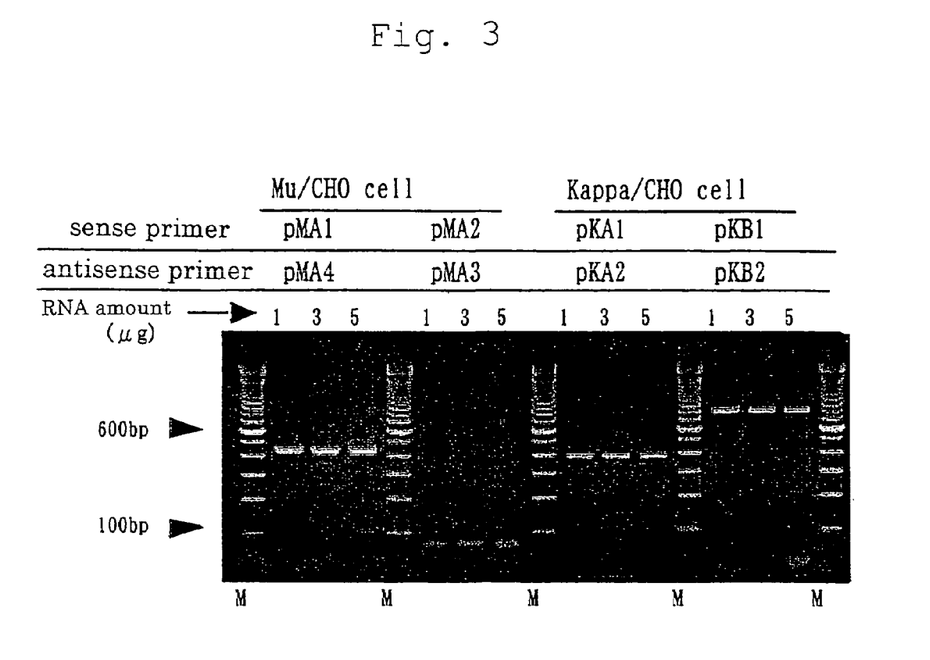
FIG. 3 is a diagram showing amplification of DNAs by reverse transcriptase-PCR (RT-PCR) method using individual primer set of positive control cell Mu/CHO or Kappa/CHO.

Initially, total RNA was extracted from the positive control Mu/CHO or Kappa/CHO and was subjected to RT-PCR, which also served as examination of the optimum amount of RNA in an RT reaction. In combinations of primers pMA1/pMA4 and pKA1/pKA2, PCR was performed for 30 cycles of cyclic reactions comprising a thermal denaturation reaction at 95° C. for 30 seconds, an annealing reaction at 65° C. for 30 seconds, and an elongation reaction at 72° C. for 30 seconds, in this order. In combinations of primers pMA2/pMA3 and pKB1/pKB2, PCR was performed for 30 cycles of cyclic reactions comprising a thermal denaturation reaction at 95° C. for 30 seconds, an annealing reaction at 55° C. for 30 seconds, and an elongation reaction at 72° C. for 30 seconds, in this order. In the reaction, DNA of a target size was observed as a single band as a result of DNA amplification as shown in FIG. 3, indicating that the expression of each receptor in the positive control can be analyzed. The symbol "M" in the figure represents a DNA size marker. Each band constitutes a 100-bp ladder. The density of each band did not differ with varying RNA amount, and the amount of the template total RNA in the following procedures was therefore set at 1 μg, which is a conventionally employed amount. In the RT-PCR, no DNA amplification was observed when RNA of the negative control (−)/CHO was used as a template.

Example 2

[Diagnosis and Therapy of Pruritus through Determination of Opioid Peptides]

(1) Diagnosis of Pruritus through Determination of Opioid Peptides in Human Plasma Peripheral blood was respectively collected from healthy adults and 37 patients with hemodialysis who periodically undergo maintenance dialysis, and was separated to serum and blood cells. Each sample was then subjected to measurement of blood opioid concentrations (β-endorphin, Leu-enkephalin, and dynorphin A), degrees of expression of receptors thereof, and blood factors (histamine, serotonin, intact PTH, and eosinophil basic protein) that are supposed to be involved in itching. The opioids in blood were measured using an RIA kit available from Peninsula Laboratories (U.S.A.). The histamine, serotonin, intact PTH, and eosinophil basic protein were determined by fluorescence method, high performance liquid chromatography (HPLC), immunoradiometric assay (IRMA), and radioimmunoassay (RIA), respectively. Peripheral blood available from 12 healthy adults was used as a control group.

Of the patients with maintenance dialysis, the measured blood levels of β-endorphin (μ-receptor agonistic substance) were 23, 28, and 29 pg/mL in patients without itching (n=19), patients with moderate itching (n=8), and patients with severe itching (n=10), respectively. The blood levels had correlation with the severity of itching. The level of dynorphin A (κ-receptor agonistic substance) in the patients with dialysis was decreased as compared with that of healthy adults, 12 pg/mL. The ratios of β-endorphin to dynorphin A were 2.2, 2.5, 2.8, and 3.6 in the healthy adults, patients without itching, patients with moderate itching, and patients with severe itching, respectively. Specifically, the ratio of β-endorphin to dynorphin A was increased with an increasing severity of itching. In contrast, the other itching-associated factors exhibited no correlation with the severity of itching.

(2) Measurement of Degree of Expression of Opioid Receptor on Human Peripheral Blood Each of peripheral blood of healthy adults and patients with dialysis was collected according to a conventional technique using EDTA and was centrifuged at 3000 rpm at 4° C. for 5 minutes to thereby remove a plasma fraction. The remainder blood cell fraction was diluted with PBS about twofold and was carefully superposed onto 4 mL of Separate-L (trade name; available from MUTO Pure Chemicals Co., Ltd.) in a 15-mL centrifuging tube. The blood cell fraction was then centrifuged at 1000 rpm to 1200 rpm at 20° C. for 30 to 40 minutes to thereby separate a peripheral blood mononuclear cell (PBMC). The separated PBMC was washed twice with PBS by centrifugation to yield a sample. Total RNA was extracted from the PBMC sample by the AGPC method, and using 1 μg of the total RNA as a template, an RT reaction was performed to yield cDNA. The prepared cDNA as a template was subjected to PCR with individual primers of μ- and κ-opioid receptors. After investigations on various conditions, DNA was amplified using an optimum primer combination under PCR conditions that can yield the best result. Specifically, a combination of pMA1 and pMA4 primers was employed for the μ-receptor, and a combination of pKA1 and pKA2 primers was employed for the κ-receptor. The PCR was performed according to the hot start method. That is, after a reaction at 94° C. for 5 minutes (hot start method), the sample was subjected to 35 cycles of cyclic reactions comprising a thermal denaturation reaction at 95° C. for 30 seconds, an annealing reaction at 68° C. (μ-receptor) or at 54° C. (κ-receptor) for 30 seconds, and an elongation reaction at 72° C. for 30 seconds, in this order. The resulting amplified DNAs were analyzed through electrophoresis. Based on the intensities of the resulting electrophoresis bands, "strong expression", "weak expression", and "no expression" were respectively rated as "+", "±", and "−". The degrees of expression of the μ- and κ-receptors were compared in individual subjects to find that the expression of the κ-receptor has the advantage over that of the μ-receptor in the healthy adults and, in contrast, the expression of the μ-receptor is equivalent to that of the κ-receptor in the patients with itching, indicating that the expression of the μ-receptor is relatively increased, as shown in Table 3.

TABLE 3

| Subject group | μ > κ | μ = κ | μ < κ |
|---|---|---|---|
| Healthy adult (without itching) (n = 10) | 0% | 20% | 80% |
| Patient with mild itching (n = 16) | 0% | 100% | 0% |
| Patient with moderate itching (n = 15) | 0% | 100% | 0% |
| Patient with severe itching (n = 9) | 0% | 100% | 0% |

(3) Therapy of Itching with κ-Opioid Agonist

Based on the results in the above (1) and (2), four patients were selected from a group to which conventional antihistaminic agents and antiallergic agents were inefficient and who constantly complained of severe itching. One capsule of a κ-opioid agonist 17-cyclopropylmethyl-3, 14β-dihydroxy-4,5α-epoxy-6β-(N-methyl-trans-3-(3-furyl)acrylamide) morphinan hydrochloride capsule (10 μg/body) was administered to each of the selected patients. In all the administered patients, itching was relieved after two hours from the administration, and the antipruritic effect continued until 24 hours from the administration. To quantitatively determine the severity of itching, visual analogue scale (VAS) was employed, in which the severity of itching was determined on a straight line of 0 to 100 mm where no itching was rated as "0" and the supposable most severe itching was rated as "100". As a mean of the four subjects, the VAS was 75 mm before administration but it was 0 mm after 4 to 24 hours from the administration.

These results indicate that, as diagnosis, opioids are involved in intractable itching which is a problem in patients with chronic renal failure or hemodialysis and that the administration of a κ-opioid agonist, which is believed to have antipruritic effect, can treat or relive itching.

Accordingly, the invented method for examination is a useful method to select a therapy of pruritus. Specifically, the invented method for examination can determine whether opioids are involved in pruritic diseases and can determine whether the therapy with an opioid agonistic and/or antagonistic antipruritus agent is appropriate or not.

Other embodiments and variations will be obvious to those skilled in the art, and this invention is not to be limited to the specific matters stated above.

What is claimed is:

1. A method for examining a pruritic disease to diagnose opioid-based pruritis, comprising the steps of:
   measuring concentrations of κ-opioid peptides and μ-opioid peptides, in serum,
   calculating the ratio of said concentrations of μ-opioid peptides to the concentration of κ-opioid peptides,
   comparing said calculated ratio to a corresponding ratio in non-pruritic patients; and
   diagnosing opioid-based pruritis where said calculated ratio is greater than said corresponding ratio.

2. The method according to claim 1, wherein said μ-opioid peptide to be measured is β-endorphin and said κ-opioid peptide is dynorphin A.

3. The method according to claim 1, wherein said pruritic disease is selected from the group consisting of pruritus with atopic dermatitis, neurodermatitis, contact dermatitis, seborrheic dermatitis, autosensitization dermatitis, caterpillar dermatitis, asteatosis, senile pruritus, insect bite, hyperesthesia optica, urticaria, prurigo, herpes, impetigo, eczema, tinea, lichen, psoriasis, scabies, acne vulgaris, malignant tumor, diabetes, hepatic disease, and renal failure.

4. The method according to claim 1, wherein said pruritic disease is selected from the group consisting of atopic dermatitis, and renal failure.

\* \* \* \* \*

SEQUENCE LISTING

<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ggtactggga aaacctgctg aagatctgtg                                    30

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
tgctggactc ccattcacat t                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
agtctggaac gtagtttctg g                                    21

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ggtctctagt gttctgacca attcgagtgg                           30

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
aaagtcaggg aagacgtcga tgtc                                 24

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gagagctcgc ggcgcgtcta cttgatgaat tcctgg                    36

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gaatgggatt caggctactg ttgg                                 24

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggaagcttga attcggtaag caggatcctg aactg                     35